(12) United States Patent
Gordon et al.

(10) Patent No.: US 8,802,149 B2
(45) Date of Patent: *Aug. 12, 2014

(54) SYSTEMS AND PROCESSES FOR SPRAY DRYING HYDROPHOBIC AND HYDROPHILIC COMPONENTS

(75) Inventors: Marc S. Gordon, Sunnyvale, CA (US); Andrew Clark, Half Moon Bay, CA (US); Thomas K. Brewer, Walnut Creek, CA (US)

(73) Assignee: Novartis Pharma AG, Basel (CH)

( * ) Notice: Subject to any disclaimer, the term of this patent is extended or adjusted under 35 U.S.C. 154(b) by 571 days.

This patent is subject to a terminal disclaimer.

(21) Appl. No.: 12/469,634

(22) Filed: May 20, 2009

(65) Prior Publication Data

US 2009/0285905 A1    Nov. 19, 2009

Related U.S. Application Data

(63) Continuation of application No. 10/403,548, filed on Mar. 31, 2003, now abandoned, which is a continuation of application No. 10/072,407, filed on Feb. 8, 2002, now Pat. No. 6,572,893, which is a continuation of application No. 09/528,758, filed on Mar. 17, 2000, now Pat. No. 6,365,190, which is a continuation of application No. 08/999,097, filed on Dec. 29, 1997, now Pat. No. 6,077,543.

(60) Provisional application No. 60/034,837, filed on Dec. 31, 1996.

(51) Int. Cl.
*A61K 9/14*    (2006.01)
*A61K 9/12*    (2006.01)

(52) U.S. Cl.
USPC ............. 424/489; 424/45; 424/46; 424/499

(58) Field of Classification Search
None
See application file for complete search history.

(56) References Cited

U.S. PATENT DOCUMENTS

| | | |
|---|---|---|
| 2,598,525 A | 4/1950 | Fox |
| 3,362,405 A | 1/1968 | Hazel |
| 3,425,600 A | 2/1969 | Abplanalp |
| 3,674,901 A | 7/1972 | Sheperd et al. |
| 3,770,207 A | 11/1973 | Muller et al. |
| 3,790,079 A | 2/1974 | Berglund et al. |

(Continued)

FOREIGN PATENT DOCUMENTS

| | | |
|---|---|---|
| CA | 2136704 | 5/1995 |
| DE | 1 078 283 | 6/1958 |

(Continued)

OTHER PUBLICATIONS

Barj et al. "Submicronic MgAl2O4 Powder Synthesis in Supercritical Ethanol." J. of Materials Sci. vol. 27. No. B p. 2187-2192 (1992).

(Continued)

*Primary Examiner* — Lakshmi Channavajjala
(74) *Attorney, Agent, or Firm* — Janah & Associates, P.C.

(57) ABSTRACT

Methods for preparing dry powders having hydrophobic and hydrophilic components comprise combining solutions of the components and spray drying them simultaneously in a spray dryer. The hydrophilic and hydrophobic component are separately dissolved in separate solvents and directed simultaneously through a nozzle, usually a coaxial nozzle, into the spray dryer. The method provides dry powders having relatively uniform characteristics.

31 Claims, 3 Drawing Sheets

(56) References Cited

U.S. PATENT DOCUMENTS

| | | |
|---|---|---|
| 3,825,188 A | 7/1974 | Doering |
| 3,921,637 A | 11/1975 | Bennie et al. |
| 3,956,009 A | 5/1976 | Lundquist et al. |
| 3,964,483 A | 6/1976 | Mathes |
| 3,991,304 A | 11/1976 | Hillsman |
| 3,991,761 A | 11/1976 | Cocozza |
| 3,994,421 A | 11/1976 | Hansen |
| 4,035,317 A | 7/1977 | Gershberg |
| 4,036,223 A | 7/1977 | Obert |
| 4,052,255 A | 10/1977 | Hackbarth et al. |
| 4,069,819 A | 1/1978 | Valentini et al. |
| 4,098,273 A | 7/1978 | Glenn |
| 4,105,027 A | 8/1978 | Lundquist |
| 4,127,235 A | 11/1978 | Klaile et al. |
| 4,153,689 A | 5/1979 | Hirai et al. |
| 4,192,309 A | 3/1980 | Poulsen |
| 4,211,769 A | 7/1980 | Okada et al. |
| 4,221,339 A | 9/1980 | Yoshikawa |
| 4,227,522 A | 10/1980 | Carris |
| 4,249,526 A | 2/1981 | Dean et al. |
| 4,253,468 A | 3/1981 | Lehmbeck |
| 4,261,793 A | 4/1981 | Nakamura et al. |
| 4,268,460 A | 5/1981 | Boiarski et al. |
| 4,294,624 A | 10/1981 | Veltman |
| 4,294,829 A | 10/1981 | Suzuki |
| 4,305,210 A | 12/1981 | Christensen et al. |
| 4,338,931 A | 7/1982 | Cavazza |
| 4,446,862 A | 5/1984 | Baum et al. |
| 4,452,239 A | 6/1984 | Malem |
| 4,476,804 A | 10/1984 | Glatt et al. |
| 4,484,577 A | 11/1984 | Sackner et al. |
| 4,486,435 A | 12/1984 | Schmidt et al. |
| 4,503,035 A | 3/1985 | Pestka et al. |
| 4,534,343 A | 8/1985 | Nowacki et al. |
| 4,540,602 A | 9/1985 | Motoyama et al. |
| 4,590,206 A | 5/1986 | Forrester et al. |
| 4,613,500 A | 9/1986 | Suzuki et al. |
| 4,624,251 A | 11/1986 | Miller |
| 4,627,432 A | 12/1986 | Newell et al. |
| 4,649,911 A | 3/1987 | Knight et al. |
| 4,659,696 A | 4/1987 | Hirai et al. |
| 4,670,419 A | 6/1987 | Uda et al. |
| 4,698,328 A | 10/1987 | Neer et al. |
| 4,702,799 A | 10/1987 | Tuot |
| 4,721,709 A | 1/1988 | Seth et al. |
| 4,739,754 A | 4/1988 | Shaner |
| 4,748,034 A | 5/1988 | de Rham |
| 4,760,093 A | 7/1988 | Blank et al. |
| 4,778,054 A | 10/1988 | Newell et al. |
| 4,784,878 A | 11/1988 | Haak |
| 4,790,305 A | 12/1988 | Zoltan et al. |
| 4,794,167 A | 12/1988 | Lindner et al. |
| 4,807,814 A | 2/1989 | Douche et al. |
| 4,811,731 A | 3/1989 | Newell et al. |
| 4,818,424 A | 4/1989 | Evans et al. |
| 4,819,629 A | 4/1989 | Jonson |
| 4,823,784 A | 4/1989 | Bordoni et al. |
| 4,828,844 A * | 5/1989 | Rontgen-Odenthal et al. ............ 424/489 |
| 4,833,125 A | 5/1989 | Neer et al. |
| 4,835,187 A | 5/1989 | Reuter et al. |
| 4,866,051 A | 9/1989 | Hunt et al. |
| 4,871,489 A | 10/1989 | Ketcham |
| 4,884,565 A | 12/1989 | Cocozza |
| 4,889,114 A | 12/1989 | Kladders |
| 4,898,781 A | 2/1990 | Onouchi et al. |
| 4,907,583 A | 3/1990 | Wetterlin et al. |
| 4,919,853 A | 4/1990 | Alvarez et al. |
| 4,926,852 A | 5/1990 | Zoltan et al. |
| 4,942,544 A | 7/1990 | McIntosh et al. |
| 4,946,828 A | 8/1990 | Markussen |
| 4,952,402 A | 8/1990 | Sparks et al. |
| 4,968,607 A | 11/1990 | Dower et al. |
| 4,984,158 A | 1/1991 | Hillsman |
| 4,995,385 A | 2/1991 | Valentini et al. |
| 4,999,189 A | 3/1991 | Kogan et al. |
| 5,000,888 A | 3/1991 | Kilbride, Jr. et al. |
| 5,009,367 A | 4/1991 | Nielsen |
| 5,011,678 A | 4/1991 | Wang et al. |
| 5,015,423 A | 5/1991 | Eguchi et al. |
| 5,017,372 A | 5/1991 | Hastings |
| 5,026,550 A | 6/1991 | Aeschbach et al. |
| 5,027,806 A | 7/1991 | Zoltan et al. |
| 5,033,463 A | 7/1991 | Cocozza |
| 5,035,237 A | 7/1991 | Newell et al. |
| 5,038,769 A | 8/1991 | Krauser |
| 5,042,975 A | 8/1991 | Chien et al. |
| 5,048,514 A | 9/1991 | Ramella |
| 5,049,388 A | 9/1991 | Knight et al. |
| 5,064,501 A | 11/1991 | Boersen |
| 5,066,522 A | 11/1991 | Cole et al. |
| 5,076,097 A | 12/1991 | Zarrin et al. |
| 5,081,228 A | 1/1992 | Dower et al. |
| 5,093,316 A | 3/1992 | Lezdey et al. |
| 5,098,893 A | 3/1992 | Franks et al. |
| 5,099,833 A | 3/1992 | Michaels |
| 5,106,659 A | 4/1992 | Hastings et al. |
| 5,113,855 A | 5/1992 | Newhouse |
| 5,130,137 A | 7/1992 | Crowley, Jr. |
| 5,139,016 A | 8/1992 | Waser |
| 5,161,524 A | 11/1992 | Evans |
| 5,178,878 A | 1/1993 | Wehling et al. |
| 5,180,812 A | 1/1993 | Dower et al. |
| 5,186,164 A | 2/1993 | Raghuprasad |
| 5,196,575 A | 3/1993 | Sebastian |
| 5,200,399 A | 4/1993 | Wettlaufer et al. |
| 5,204,108 A | 4/1993 | Illum |
| 5,206,219 A | 4/1993 | Desai |
| 5,206,306 A | 4/1993 | Shen |
| 5,219,575 A | 6/1993 | Van Bommel et al. |
| 5,221,731 A | 6/1993 | Weymans et al. |
| 5,230,884 A | 7/1993 | Evans et al. |
| 5,232,707 A | 8/1993 | Lokensgard |
| 5,235,969 A | 8/1993 | Bellm |
| 5,254,330 A | 10/1993 | Ganderton et al. |
| 5,260,306 A | 11/1993 | Boardman et al. |
| 5,269,980 A | 12/1993 | Levendis et al. |
| 5,279,708 A | 1/1994 | Wood et al. |
| 5,290,765 A | 3/1994 | Wettlaufer et al. |
| 5,295,479 A | 3/1994 | Lankinen |
| 5,302,581 A | 4/1994 | Sarin et al. |
| 5,309,900 A | 5/1994 | Knoch et al. |
| 5,320,094 A | 6/1994 | Laube et al. |
| 5,320,714 A | 6/1994 | Brendel |
| 5,331,953 A | 7/1994 | Andersson et al. |
| 5,348,730 A | 9/1994 | Greenleaf et al. |
| 5,354,562 A | 10/1994 | Platz et al. |
| 5,354,934 A | 10/1994 | Pitt et al. |
| 5,356,636 A | 10/1994 | Schneider et al. |
| 5,364,838 A | 11/1994 | Rubsamen |
| 5,376,359 A | 12/1994 | Johnson |
| 5,376,386 A | 12/1994 | Ganderton et al. |
| 5,384,133 A | 1/1995 | Boyes et al. |
| 5,458,135 A | 10/1995 | Patton et al. |
| 5,482,927 A | 1/1996 | Maniar et al. |
| 5,487,378 A | 1/1996 | Robertson et al. |
| 5,506,203 A | 4/1996 | Backstrom et al. |
| 5,510,118 A | 4/1996 | Bosch et al. |
| 5,518,187 A | 5/1996 | Bruno et al. |
| 5,518,709 A | 5/1996 | Sutton et al. |
| 5,518,998 A | 5/1996 | Backstrom et al. |
| 5,534,270 A | 7/1996 | De Castro |
| 5,542,935 A | 8/1996 | Unger et al. |
| 5,580,856 A | 12/1996 | Prestrelski et al. |
| 5,607,697 A | 3/1997 | Alkire et al. |
| 5,607,915 A | 3/1997 | Patton |
| 5,609,919 A | 3/1997 | Yuan et al. |
| 5,622,657 A | 4/1997 | Takada et al. |
| 5,624,530 A | 4/1997 | Sadykhov et al. |
| 5,628,937 A | 5/1997 | Oliver et al. |
| 5,639,475 A | 6/1997 | Bettman et al. |
| 5,648,096 A | 7/1997 | Gander et al. |
| 5,651,990 A | 7/1997 | Takada et al. |
| 5,667,806 A | 9/1997 | Kanter |

(56) References Cited

U.S. PATENT DOCUMENTS

| | | | |
|---|---|---|---|
| 5,687,905 A | 11/1997 | Tsai | |
| 5,707,644 A | 1/1998 | Illum | |
| 5,716,558 A | 2/1998 | Nielsen et al. | |
| 5,723,269 A | 3/1998 | Akagi et al. | |
| 5,727,333 A | 3/1998 | Folan | |
| 5,740,794 A | 4/1998 | Smith et al. | |
| 5,741,478 A | 4/1998 | Osborne et al. | |
| 5,770,559 A | 6/1998 | Manning et al. | |
| 5,776,491 A | 7/1998 | Allen, Jr. et al. | |
| 5,785,049 A | 7/1998 | Smith et al. | |
| 5,800,598 A | 9/1998 | Chein et al. | |
| 5,807,576 A | 9/1998 | Allen, Jr. et al. | |
| 5,807,578 A | 9/1998 | Acosta-Cuello et al. | |
| 5,855,913 A | 1/1999 | Hanes et al. | |
| 5,874,029 A | 2/1999 | Subramaniam et al. | |
| 5,874,064 A | 2/1999 | Edwards et al. | |
| 5,916,596 A | 6/1999 | Desai et al. | |
| 5,922,253 A | 7/1999 | Herbert et al. | |
| 5,924,216 A | 7/1999 | Takahashi | |
| 5,952,008 A | 9/1999 | Backstrom et al. | |
| 5,957,848 A | 9/1999 | Sutton et al. | |
| 5,964,416 A | 10/1999 | Jaeger et al. | |
| 5,970,974 A | 10/1999 | Van Der Linden et al. | |
| 5,972,388 A | 10/1999 | Sakon et al. | |
| 5,976,574 A * | 11/1999 | Gordon | 424/489 |
| 5,981,474 A | 11/1999 | Manning et al. | |
| 5,985,248 A * | 11/1999 | Gordon et al. | 424/46 |
| 5,985,309 A | 11/1999 | Edwards et al. | |
| 5,993,805 A | 11/1999 | Sutton et al. | |
| 5,997,848 A | 12/1999 | Patton et al. | |
| 6,000,241 A | 12/1999 | Ranade et al. | |
| 6,001,336 A * | 12/1999 | Gordon | 424/46 |
| 6,015,546 A | 1/2000 | Sutton et al. | |
| 6,017,310 A | 1/2000 | Johnson et al. | |
| 6,022,525 A | 2/2000 | Sutton et al. | |
| 6,045,828 A * | 4/2000 | Bystrom et al. | 424/489 |
| 6,051,256 A * | 4/2000 | Platz et al. | 424/489 |
| 6,051,257 A | 4/2000 | Kodas et al. | |
| 6,077,543 A | 6/2000 | Gordon et al. | |
| 6,080,721 A * | 6/2000 | Patton | 514/11.8 |
| 6,117,455 A | 9/2000 | Takada et al. | |
| 6,119,953 A | 9/2000 | Ganan-Calvo et al. | |
| 6,123,924 A | 9/2000 | Mistry et al. | |
| 6,136,295 A | 10/2000 | Edwards et al. | |
| 6,149,941 A | 11/2000 | Schwarz et al. | |
| 6,153,129 A | 11/2000 | Herbert et al. | |
| 6,156,511 A | 12/2000 | Schatz et al. | |
| 6,165,511 A | 12/2000 | Schwarz et al. | |
| 6,174,469 B1 | 1/2001 | Ganan-Calvo | |
| 6,197,835 B1 | 3/2001 | Ganan-Calvo | |
| 6,223,455 B1 | 5/2001 | Chickering, III et al. | |
| 6,241,159 B1 | 6/2001 | Ganan-Calvo et al. | |
| 6,258,341 B1 | 7/2001 | Foster et al. | |
| 6,290,991 B1 | 9/2001 | Roser et al. | |
| 6,308,434 B1 | 10/2001 | Chickering, III et al. | |
| 6,315,983 B1 | 11/2001 | Eistetter | |
| 6,316,029 B1 | 11/2001 | Jain et al. | |
| 6,331,290 B1 | 12/2001 | Morgan | |
| 6,331,310 B1 | 12/2001 | Roser et al. | |
| 6,365,190 B1 * | 4/2002 | Gordon et al. | 424/489 |
| 6,372,258 B1 | 4/2002 | Platz et al. | |
| 6,383,810 B2 | 5/2002 | Fike et al. | |
| 6,387,410 B1 | 5/2002 | Woolfe et al. | |
| 6,416,739 B1 | 7/2002 | Rogerson et al. | |
| 6,423,344 B1 | 7/2002 | Platz et al. | |
| 6,451,349 B1 | 9/2002 | Robinson et al. | |
| 6,455,028 B1 | 9/2002 | Wulffhart et al. | |
| 6,503,480 B1 | 1/2003 | Edwards et al. | |
| 6,560,897 B2 | 5/2003 | Chickering, III et al. | |
| 6,565,885 B1 | 5/2003 | Tarara et al. | |
| 6,572,893 B2 * | 6/2003 | Gordon et al. | 424/489 |
| 6,582,728 B1 | 6/2003 | Platz et al. | |
| 6,592,904 B2 | 7/2003 | Platz et al. | |
| 6,656,492 B2 | 12/2003 | Kajiyama et al. | |
| 6,660,382 B2 | 12/2003 | Nouri et al. | |
| 6,743,413 B1 | 6/2004 | Schultz et al. | |
| 6,884,408 B2 | 4/2005 | Rabinowitz et al. | |
| 2002/0071871 A1 | 6/2002 | Snyder et al. | |
| 2002/0081266 A1 | 6/2002 | Woolfe et al. | |
| 2002/0175225 A1 | 11/2002 | Boersen et al. | |
| 2003/0086970 A1 | 5/2003 | Woolfe et al. | |
| 2003/0124193 A1 | 7/2003 | Snyder et al. | |
| 2003/0203036 A1 | 10/2003 | Gordon et al. | |
| 2003/0215514 A1 | 11/2003 | Platz et al. | |

FOREIGN PATENT DOCUMENTS

| | | |
|---|---|---|
| DE | 3501983 | 7/1985 |
| DE | 3806537 | 9/1989 |
| DE | 4329204 | 3/1995 |
| EP | 0002018 | 5/1979 |
| EP | 0 072046 | 2/1983 |
| EP | 0 122036 | 10/1984 |
| EP | 0 164311 | 12/1985 |
| EP | 0237507 | 9/1987 |
| EP | 0260971 | 3/1988 |
| EP | 0 344375 | 12/1989 |
| EP | 0347779 | 12/1989 |
| EP | 0 360340 | 3/1990 |
| EP | 0 383569 | 8/1990 |
| EP | 0408801 | 1/1991 |
| EP | 0 461930 | 12/1991 |
| EP | 0467172 | 1/1992 |
| EP | 0468914 | 1/1992 |
| EP | 4 69725 | 2/1992 |
| EP | 0492797 | 6/1992 |
| EP | 0506293 | 9/1992 |
| EP | 5 12693 | 11/1992 |
| EP | 0464171 | 12/1992 |
| EP | 0535937 | 4/1993 |
| EP | 0580428 | 1/1994 |
| EP | 6 28331 | 12/1994 |
| EP | 0655237 | 5/1995 |
| EP | 6 74541 | 10/1995 |
| EP | 0677332 | 10/1995 |
| EP | 6 81843 | 11/1995 |
| EP | 0 709085 | 5/1996 |
| EP | 0 972526 | 1/2000 |
| EP | 1 004349 | 5/2000 |
| EP | 1 022020 | 7/2000 |
| EP | 0611567 | 8/2002 |
| FR | 2257351 | 8/1975 |
| GB | 473471 | 10/1937 |
| GB | 621785 | 4/1949 |
| GB | 1112553 | 5/1968 |
| GB | 1527605 | 8/1975 |
| GB | 2 105189 | 3/1983 |
| JP | 55-167218 | 12/1980 |
| JP | 5732215 | 2/1982 |
| JP | 05-194200 | 3/1993 |
| JP | 5-194274 | 8/1993 |
| JP | 6-293636 | 10/1994 |
| JP | 07-187996 | 7/1995 |
| JP | 8-92098 | 4/1996 |
| JP | 8-505152 | 6/1996 |
| JP | 8-301762 | 11/1996 |
| JP | 2000-510471 | 8/2000 |
| NL | 7712041 | 5/1979 |
| SU | 0628930 | 10/1978 |
| SU | 1003926 | 1/1979 |
| WO | WO 88/04556 | 6/1988 |
| WO | WO 88/07870 | 10/1988 |
| WO | WO 88/09163 | 12/1988 |
| WO | WO90/07351 | 7/1990 |
| WO | WO90/09780 | 9/1990 |
| WO | WO 90/11139 | 10/1990 |
| WO | WO90/15635 | 12/1990 |
| WO | WO91/02545 | 3/1991 |
| WO | WO91/02558 | 3/1991 |
| WO | WO 91/16882 | 11/1991 |
| WO | WO 92/18164 | 10/1992 |
| WO | WO 93/02712 | 2/1993 |
| WO | WO93/07465 | 4/1993 |
| WO | WO93/09832 | 5/1993 |

(56) References Cited

FOREIGN PATENT DOCUMENTS

| WO | WO 93/25198 | 12/1993 |
|----|----|----|
| WO | WO 94/07514 | 4/1994 |
| WO | WO94/08552 | 4/1994 |
| WO | WO 94/08627 | 4/1994 |
| WO | WO 94/15636 | 7/1994 |
| WO | WO 94/21232 | 9/1994 |
| WO | WO95/00127 | 1/1995 |
| WO | WO95/00128 | 1/1995 |
| WO | WO 95/08987 | 4/1995 |
| WO | WO 95/11015 | 4/1995 |
| WO | WO 95/13864 | 5/1995 |
| WO | WO 95/23613 | 9/1995 |
| WO | WO 95/24183 | 9/1995 |
| WO | WO 95/31479 | 11/1995 |
| WO | WO 96/03978 | 2/1996 |
| WO | WO 96/05809 | 2/1996 |
| WO | WO 96/09085 | 3/1996 |
| WO | WO 96/09814 | 4/1996 |
| WO | WO 96/11580 | 4/1996 |
| WO | WO 96/15814 | 5/1996 |
| WO | WO 96/32096 | * 10/1996 |
| WO | WO 96/32116 | 10/1996 |
| WO | WO 96/32149 | 10/1996 |
| WO | WO 96/38153 | 12/1996 |
| WO | WO96/40076 | 12/1996 |
| WO | WO97/03649 | 2/1997 |
| WO | WO 97/26863 | 7/1997 |
| WO | WO 97/28788 | 8/1997 |
| WO | WO 97/36574 | 10/1997 |
| WO | WO 97/36578 | 10/1997 |
| WO | WO 97/41833 | 11/1997 |
| WO | WO 97/44067 | 11/1997 |
| WO | WO 98/01228 | 1/1998 |
| WO | WO 98/29096 | 7/1998 |
| WO | WO 98/29098 | 7/1998 |
| WO | WO 98/31346 | 7/1998 |
| WO | WO98/36888 | 8/1998 |
| WO | WO 98/47493 | 10/1998 |
| WO | WO 99/10419 | 4/1999 |
| WO | WO 99/16422 | 4/1999 |
| WO | WO 99/17742 | 4/1999 |
| WO | WO 99/30834 | 6/1999 |
| WO | WO 99/31019 | 6/1999 |
| WO | WO 99/32083 | 7/1999 |
| WO | WO99/61006 | 12/1999 |
| WO | WO99/64014 | 12/1999 |
| WO | WO 00/00176 | 1/2000 |
| WO | WO 00/09084 | 2/2000 |
| WO | WO 00/10541 | 3/2000 |
| WO | WO 00/12278 | 3/2000 |
| WO | WO 00/13668 | 3/2000 |
| WO | WO 00/66256 | 11/2000 |
| WO | WO 00/76673 | 12/2000 |
| WO | WO 01/03673 | 1/2001 |
| WO | WO 01/13885 | 3/2001 |
| WO | WO 01/15664 | 3/2001 |
| WO | WO 01/45731 | 6/2001 |
| WO | WO01/49263 | 7/2001 |
| WO | WO 01/64188 | 9/2001 |
| WO | WO 01/87278 | 11/2001 |
| WO | WO 02/09669 | 2/2002 |
| WO | WO 02/15876 | 2/2002 |
| WO | WO 02/15880 | 2/2002 |
| WO | WO 02/078675 | 10/2002 |
| WO | WO02/078675 | 10/2002 |
| WO | WO 03/000202 | 1/2003 |
| WO | WO 03/070225 | 8/2003 |
| WO | WO 03/074029 | 9/2003 |

OTHER PUBLICATIONS

Bjork, E. et al., "Degradable Starch Microspheres As a Nasal Delivery System for Insulin." International Journal of Pharmaceutics. 1988. vol. 47. pp. 233-238.

Bodmeier, et al., "Preparation of Biodegradable Poly(+)lactide Microparticles Using a Spray-Drying Technique", J. Pharm. Pharmocol. 1988, 40:, p. 754-757.

Bohnet. Matthias, "Calculation and Design of Gas/Solid-Injectors," Powder Tech, 1984. pp. 302-313.

Brandenberger, "A New Multinozzle Encapsulation/Immobilisation System to Produce Uniform Beads of Alginate", Journal of Biotechnology, vol. 63, No. 1, p. 73-80 (1998).

Budrik, G. K. et al.. "Ejector Feeders for Pneumatic Transport Systems," Chemical Petroleum Engineering. Sep.-Oct. 1978. vol. 14, Nos. 9-10. pp. 9-10.

Byron, P. R. et al. "Drug Delivery Via the Respiratory Tract," Journal or Aerosol Medicine, 1994. vol. 7, No. 1. pp. 49-75.

Chien, Y. W. et al.. "Intranasal Drug Delivery for Systemic Medications," Critical Reviews in Therapeutic Drug Carries Systems. 1987, vol. 4, Issue 2, pp. 67-92. (1 Page).

Colthorpe P. et al., "The pharmacokinetics of pulmonary-delivered insulin: a comparison of intratrachaal and aerosol administration to the rabbit.," Pharmaceutical Research. 1992. vol. 9. No. 6, pp. 764-768. (1 page).

de Boer, et al., "Air classifier technology (ACT) in dry powder inhalation Part 2. The effect of lactose carrier surface properties on the drug-to-carrier interaction in adhesive mixtures for inhalation", International Journal of Pharmaceutics, vol. 260, 2003, Elsevier Science B.V., pp. 201-216.

Duchateau. G. etal . "Bile Salts and Intranasal Drug Absorption", International Journal of Pharmaceutics, 1986. vol. 31. pp. 193-199.

Elliott, et: al . "Parenteral Absorption of insulin From the Lung in Diabetic Children." Aust.Paediatr. J. 1987, vol. 23. pp. 293-297.

EP Search Report dated Dec. 16, 2005 for Application No. 97926420.7.

EPO Communication dated May 15, 2007 for European Application No. 02776395.2.

EPO Communication dated Nov. 2, 2006 for European Application No. 97926420.7.

European Examination Report dated Jun. 11, 2008 for European Application No. 97926 420.7-1216.

Examiner's Report for Slovak Republic Patent Application No. PP 0146-2006-2001.

Ferrari, et al., "The Surface Roughness of Lactose Particles Can Be Modulated by Wet-Smoothing Using a High-Shear Mixer", AAPS PharmSciTech, Dec. 2004, vol. 5, No. 4, Article 60, (http://www.aapspharmscitech.org), pp. 1-6.

Fox, et al., "Performance of a Venturi Eductor as a Feeder in a Pneumatic Conveying System." Powder & Bulk Engineering, Mar. 1988. pp. 33-36.

Friedman. T., "Progress Toward Human Gene Therapy," Science, Jun. 16, 1989, vol. 244, pp. 1275-1281.

Gansslen, M., "Uber Inhalation Von Insulin," Klin. Wochenschr, Jan. 1925, vol. 4, p. 71. with translation included (3 pages).

Govinda Rao, A. R., "Aerosol insulin inhalation Enquiry," Indian J. Phvsiol. Pharmacol, 1959. vol. 3, pp. 161-167.

Habener. Joel F., "Parathyroid Homione: Secretion and Metabolism In Vivo," Proc. Nat. Acad. Sci. USA. Dec. 1971. vol. 68. No. 12. pp. 2986-2991.

Hastings, et al., "Clearance of Different-Sized Proteins from the Alveolar Space in Humans and Rabbits," J.Appl. Physiol., 1192, vol. 73, pp. 1310-1316. (1 page).

Hesch, R. D., Pulsatile secretion of parathyroid hormone and its action on a type I and type II PTH receptor: a hypothesis for understanding osteoporosis} Calcihed Tissue int. 1988, vol. 42. pp. 341-344.

Hubbard, Richard C. and Ronald G. Cryscal, Abstract Strategies for aerosol therapy of alpha 1-antitrypsin deficiency by the aerosol route . . . Lung. 1990, vol. 168, Supplement: 1990, Proceedings ofthe 8th Congress of SEP. Edited by H. Matthys, pp. 565-578.

Kohler, Dieter ec al., "Nicht Radioaktives Verfahren Zur Messung' Der Lung'enpermeabilitat: inhalation Von Insulin," Atemu. Lunaenkrkh. Jahraana. 1987, vol. 13. No. 5. pp. 230-232. For English Abstract see Schluter Reference.

Laube. Beth L. et al., "Preliminary study of the efficacy of insulin aerosol delivered by oral inhalation in diabetic patients." JAMA. Apr. 28, 1993, vol. 269. No. 16. pp. 2106-2109. (1 page).

(56) References Cited

OTHER PUBLICATIONS

Lee, Shih-Wei etal., "Development of an aerosol dosage form containing insulin," Journal of Pharmaceutical Sciences. vol. 65, No. 4, Apr. 1976, pp. 567-572. (1 page).
Liu, Fang-Yu et al., "Pulmonary Delivery of Free and Liposomal Insulin," Pharmaceutical Research 1993, vol. 10. No. 2. pp. 228-232.
Moses, Diabetes, vol. 32, Nov. 1983, pp. 1040-1047.
Nagai, Tsuneji et al., "Powder Dosage Form of Insulin for Nasal Administration," Journal of Controlled Release. 1984. vol. 1, pp. 15-22.
Neer, 2. M. et al.."The Use of Parathyroid Hormone Plus 1.25-Dihydroxyvitamin D to increase Trabecular Bone in Osteoporotic Men and Poscmenopausal Women," Osteoporosis. 1987, vol. 53. pp. 829-835.
Nieminen, M. M. etal., "Aerosol Deposition in Automatic Dosimeter NebUlization." Eur. J. Resir. Dis. 1987, vol. 71. PC. 145>> 152. (1 page) Partial EP Search Report dated Jan. 4, 2006 for Application No. 97926420.7.
Office Action in European Application No. 08 16 0325.
Patton, John S. et al., "(D) Routes of Delivery: Case Studies—(2) Pulmonary Delivery of Peptides and Proteins for Systemic Action," Advanced Drug Delivery Reviews. 1992. vol. 8, pp. 179-196.
Pikal, Michael et al., "Moisture Transfer From Stopper to Product and Resulting Stability Implications, Develooments in Bioloaical Standardardization. 1991.," vol. 74, International Symposium on Biological Product Freeze-Drying and Formulation, pp. 1.
Pikal, Michael J., "Polymorphisms in Pharmaceutical Solids," AAPS. Nov. 5, 1992. Annual Meeting and Expositions, San Antonio, TX. 2 pages.
Pittman, et al., "Pneumatic Conveying of Bulk Solids Using a Vacuum Aerated Feed Nozzle." Solid Handling Conference Paper C4. Jun. 10-12, 1985 Thames Polytechnic London, United Kingdom, pp. C41-CS1.
Prusse, et al., "Production of Spherical Beads by Jet Cutting", 23 ed, vol. 12, Chem. Eng. Technol. (2000).
Rosenfeld, et al., "Adenovirus-Mediated Transfer of a Recombinant a—1-Antitrypsin Gene to the Lung Epithelium in Vivo," Science. vol. 252, Apr. 19, 1991. pp. 431-434.
Ryden, Lena et al., "Effect of—Polymers and Microspheres on the Nasal Absorption of Insulin in Rats," International Journal of Pharmaceutics. 1992, vol. 83, pp. 1-10.
Sakr, Farouk M., "A New Approach for Insulin Delivery Via the Pulmonary Route: Design and Pharmacokinetics in Non-Diabetic Rabbits," International Journal of Pharmaceutics. 1992, vol. 86, pp. 1-7. (1 page).
Schluter, Klaus J. et al., "Pulmonary Administration of Human insulin in Volunteers and Type I-Diabetics," Abstract Reproduction Form for Annual Meeting Program Published in Diabetes Feb. 1, 1.984. one page.
Stribling et: al., "The Mouse As a Model for Cationic Liposome-Based, Aerosolized Gene Delivery," Journal of Biopharmaceutical Sciences. 1992, 3(1./2), pp. 255-263.
Taylor, et al., "Liposomes for Drug Delivery to the Respiratory Tract", Drug Development and Industrial Pharmacy 1993, 19(1&2), p. 124-142.
Underwood, et al., "A Novel Technique for the Administration of Bronchodilator Drugs Formulated As Dry Powders to the Anaesthetized Guinea Pig," Journal of Pharmacological Methods. 1991. vol. 26. pp. 203-210.
Wigley, Frederick et al., "Insulin Across Respiratory Mucosae by Aerosol Delivery," Diabetes. 1971, vol. 20, No. 8, pp. 552-556. (1 page).
Witham, Clyde L., "Dry Dispersion With Sonic Velocity Nozzles," Workshop on Dissemination Techniques for Smoke and Obscurants Chemical Systems Laboratory. Aberdeen Proving Group. MD, Mar. 14-16, 1983, pp. 1-26.
Yoshida, H., "Absoition of Insulin Delivered to Rabbit Trachea Using Aerosol Dosage F¤ rm," Journal of Pharmaceutical Sciences. May 1979, vol. 68, No. 5, pp. 670671. (1 page).
Zholob, V. M. et al., "Effect of Injector Unit Design on the Particle Size of Atomized P0wder," 0038-5735/79/1806, 1.97.9 Plenum Publishing Corporation, pp. 352-364, Dnepropetrovsk State University, Translated from Poroshkovava Metalluraiva.
Channavajjala, Lakshmi Sarada, Office Action in U.S. Appl. No. 10/403,548, mailed Sep. 4, 2008.
Channavajjala, Lakshmi Sarada, Office Action in U.S. Appl. No. 10/403,548, mailed Feb. 25, 2008.
Channavajjala, Lakshmi Sarada, Office Action in U.S. Appl. No. 10/403,548, mailed May 18, 2006.
Channavajjala, Lakshmi Sarada, Office Action in U.S. Appl. No. 10/403,548, mailed Jul. 22, 2005.
Channavajjala, Lakshmi Sarada, Office Action in U.S. Appl. No. 10/403,548, mailed Oct. 28, 2004.
Channavajjala, Lakshmi Sarada, Office Action in U.S. Appl. No. 10/403,548, mailed Dec. 8, 2003.
European Communication, Application No. 97 954 240.4 mail date Jul. 31, 2008.
Carpenter, John F. et al., "Modes of Stabilization of a Protein by Organic Solutes During Desiccation," Cryobiology. 1988. vol. 25, pp. 459-470.
He et al., "Chitosan Microspheres Prepared by Spray Drying," International J. of Pharm. (Amsterdam), vol. 187, No. 1, o. 53-65.
Hino et al., "Development of a new type nozzle and spray-drier for industrial production of fine powders", European J. of Pharmaceutics and Biopharmaceutics (2000), vol. 49, pp. 79-85.
Masters, "The Process Stages of Spray Drying: Atomization", Spray Drying Handbook, pp. 230-247.
Bloch et al., "Dispersions of Hydrochlorothiazide and Chlorhalidone in Pentaerythritol." Pharm. Acta. Helv. (1983), 58(1):. p. 14-22.
Dialog® Abstract of German Patent Publication No. DE2209477. One page total.
Dialog® Abstract of French Patent Publication No. FR2594693. One page total.
Dialog® Abstract of Japanese Patent Publication No. JP4036233. One page total.
Dialog® Abstract of Japanese Patent Publication No. JP7101881. One page total.
Dialog® Abstract of Japanese Patent Publication No. JP7101883. One page total.
Dialog® Abstract of Japanese Patent Publication No. JP7101884. One page total.
Dialog® Abstract of Japanese Patent Publication No. JP7101882. One page total.
Dialog® Abstract of Japanese Patent Publication No. JP7242568. One page total.
Dialog® Abstract of Japanese Patent Publication No. JP8067666. One page total.
Mumenthaler et al., "Feasibility Study on Spray-Drying Protein Pharmaceuticals: Recombinant Human Growth Hormone and Tissue-Type Plasminogen Activator." Pharm Res. (1994.) 11(1):. p. 12-20.
Machado José JB et al "Solid-liquid equilibrium of α-lactose in ethanol/water" Fluid Phase Equilibria 173:121-134 (2000).
Rote Liste 1996, Abstract 24-301 Exosurf® Neonatal.
English abstract of JP5194274 (Aug. 3, 1993).
English abstract of JP8301762 (Nov. 19, 1996).

\* cited by examiner

SYSTEMS AND PROCESSES FOR SPRAY DRYING HYDROPHOBIC AND HYDROPHILIC COMPONENTS

CROSS-REFERENCE TO RELATED APPLICATIONS

This application is a continuation of U.S. Ser. No. 10/403,548, filed Mar. 31, 2003, which is a continuation of U.S. Ser. No. 10/072,407, filed Feb. 8, 2002, now U.S. Pat. No. 6,572,893, which is a continuation of U.S. Ser. No. 09/528,758, filed Mar. 17, 2000, now U.S. Pat. No. 6,365,190, which is a continuation of U.S. Ser. No. 08/999,097, filed Dec. 29, 1997, now U.S. Pat. No. 6,077,543, which claims benefit of U.S. Ser. No. 60/034,837, filed Dec. 31, 1996, which are incorporated herein by reference in their entirety.

BACKGROUND OF THE INVENTION

1. Field of the Invention

The present invention relates generally to dry powder compositions and methods for their preparation and use. In particular, the present invention relates to methods for spray drying pharmaceutical and other compositions comprising a hydrophobic drug or other component and a hydrophilic excipient or other component.

2. Description of the Related Art

Over the years, certain drugs have been sold in formulations suitable for oral inhalation (pulmonary delivery) to treat various conditions in humans. Such pulmonary drug delivery formulations are designed to be inhaled by the patient so that the active drug within the dispersion reaches the lung. It has been found that certain drugs delivered to the lung are readily absorbed through the alveolar region directly into blood circulation. Such pulmonary delivery can be effective both for systemic delivery and for localized delivery to treat diseases of the lungs.

Pulmonary drug delivery can itself be achieved by different approaches, including liquid nebulizers, aerosol-based metered dose inhalers (MDI's), and dry powder dispersion devices. Aerosol-based MDI's are losing favor because they rely on the use of chlorofluorocarbons (CFC's), which are being banned because of their adverse effect on the ozone layer. Dry powder dispersion devices, which do not rely on CFC aerosol technology, are promising for delivering drugs that may be readily formulated as dry powders.

The ability to deliver pharmaceutical compositions as dry powders, however, is problematic in certain respects. The dosage of many pharmaceutical compositions is often critical, so it is desirable that dry powder delivery systems be able to accurately, precisely, and reliably deliver the intended amount of drug. Moreover, many pharmaceutical compositions are quite expensive. Thus, the ability to efficiently formulate, process, package, and deliver the dry powders with a minimal loss of drug is critical. With dry powder drug delivery, both the delivered dose efficiency, i.e. the percentage of drug from a unit dose receptacle which is aerosolized and delivered from a delivery device, and the median particle size distribution, i.e. the deviation from the median size, are critical to the successful delivery of powders to a patient's lungs.

A particularly promising approach for the pulmonary delivery of dry powder drugs utilizes a hand-held device with a hand pump for providing a source of pressurized gas. The pressurized gas is abruptly released through a powder dispersion device, such as a venturi nozzle, and the dispersed powder made available for patient inhalation. While advantageous in many respects, such hand-held devices are problematic in a number of other respects. The particles being delivered are usually less than 5 μm in size, making powder handling and dispersion more difficult than with larger particles. The problems are exacerbated by the relatively small volumes of pressurized gas, which are available using hand-actuated pumps. In particular, venturi dispersion devices are unsuitable for difficult-to-disperse powders when only small volumes of pressurized gas are available with the handpump. Another requirement for hand-held and other powder delivery devices is efficiency. High device efficiency in delivering the drug to the patient with the optimal size distribution for pulmonary delivery is essential for a commercially viable product.

Spray drying is a conventional chemical processing unit operation used to produce dry particulate solids from a variety of liquid and slurry starting materials. The use of spray drying for the formulation of dry powder pharmaceuticals is known, but has usually been limited to spray drying of hydrophilic drugs in aqueous solutions, usually in combination with hydrophilic excipients. Many drugs, however, are hydrophobic, preventing spray drying in aqueous solutions. While spray drying of hydrophobic materials can often be accomplished using an organic solvent, the use of such nonaqueous solvents generally limits the ability to simultaneously spray dry a hydrophilic excipient.

For these reasons, it would be desirable to provide improved methods for spray drying pharmaceutical and other compositions which comprise both hydrophobic and hydrophilic components, such as hydrophobic drugs and hydrophilic excipients. Such spray drying methods should be compatible with a wide variety of hydrophobic drugs as well as conventional hydrophilic excipients, such as povidone (polyvinylpyrrolidone) and other water soluble polymers, citric acid, mannitol, pectin and other water soluble carbohydrates, and particularly with those excipients which are accepted for use in inhalation formulations, such as lactose, sodium chloride, and sodium citrate. Such spray drying methods will preferably produce particles having a uniform size distribution, with a mean particle size below 10 μm, preferably below 5 μm, and a standard deviation less than or equal to ±2 μm. Such powders should further exhibit uniform composition from batch to batch so that any tendency for particles of different compositions and/or sizes to separate in the lungs will have a reproducible impact on the therapeutic effect. Additionally, such spray drying methods should provide for dry powders which are physically and chemically stable and which have low levels of any residual organic solvents or other components which might be used in the spray drying process. At least some of the above objectives will be met by the various embodiments of the present invention which are described in detail below.

Methods for spray drying hydrophobic and other drugs and components are described in U.S. Pat. Nos. 5,000,888; 5,026,550; 4,670,419; 4,540,602; and 4,486,435. Bloch and Speison (1983) Pharm. Acta Helv 58:14-22 teaches spray drying of hydrochlorothiazide and chlorthalidone (lipophilic drugs) and a hydrophilic adjuvant (pentaerythritol) in azeotropic solvents of dioxane-water and 2-ethoxyethanol-water. A number of Japanese Patent application Abstracts relate to spray drying of hydrophilic-hydrophobic product combinations, including JP 806766; JP 7242568; JP 7101884; JP 7101883; JP 71018982; JP 7101881; and JP 4036233. Other foreign patent publications relevant to spray drying hydrophilic-hydrophobic product combinations include FR 2594693; DE 2209477; and WO 88/07870.

WO 96/09814 describes spray dried pharmaceutical powders. In particular, Example 7 describes spray drying budesonide and lactose in ethanol where the budesonide is partially soluble and the lactose is insoluble. U.S. Pat. Nos. 5,260,306; 4,590,206; GB 2 105 189; and EP 072 046 describe a method for spray drying nedocromil sodium to form small particles preferably in the range from 2 to 15 µm for pulmonary delivery. U.S. Pat. No. 5,376,386, describes the preparation of particulate polysaccharide carriers for pulmonary drug delivery, where the carriers comprise particles sized from 5 to 1000 µm. Mumenthaler et al. (1994) *Pharm. Res.* 11:12 describes recombinant human growth hormone and recombinant tissue-type plasminogen activator. WO 95/23613 describes preparing an inhalation powder of DNase by spray drying using laboratory-scale equipment. WO 91/16882 describes a method for spray drying proteins and other drugs in liposome carriers.

The following applications assigned to the assignee of the present application each describe that spray drying may be used to prepare dry powders of biological macromolecules; U.S. Ser. No. 08/644,681, filed on May 8, 1996, which was a continuation-in-part of U.S. Ser. No. 08/423,515, filed on Apr. 14, 1995; U.S. Ser. No. 08/383,475, which was a continuation-in-part of U.S. Ser. No. 08/207,472, filed on Mar. 7, 1994; U.S. Ser. No. 08/472,563, filed on Apr. 14, 1995, which was a continuation-in-part of U.S. Ser. No. 08/417,507, filed on Apr. 4, 1995, now abandoned, which was a continuation of U.S. Ser. No. 08/044,358, filed on Apr. 7, 1993, now abandoned; U.S. Ser. No. 08/232,849, filed on Apr. 25, 1994, which was a continuation of U.S. Ser. No. 07/953,397, now abandoned. WO 94/07514 claims priority from U.S. Ser. No. 07/953,397. WO 95/24183 claims priority from U.S. Ser. Nos. 08/207,472 and 08/383,475.

SUMMARY OF THE INVENTION

According to the present invention, methods for spray drying hydrophobic drugs and other materials are provided which overcome at least some of the deficiencies noted above with respect to prior spray drying processes. In particular, the spray drying methods of the present invention permit the simultaneous spray drying of the hydrophobic component with a hydrophilic component, such as a hydrophilic pharmaceutical excipient, under conditions which result in a dry powder comprising mixtures of both the hydrophilic and hydrophobic components. Although the methods of the present invention are particularly useful for forming pharmaceutical compositions where the hydrophobic component is a hydrophobic drug, usually present at from 0.01% to 95% of the powder, and the hydrophilic component is a hydrophilic excipient, usually present at from 99.99% to 5% of the powder, the methods may be applied more broadly to form dry powders comprising a variety of hydrophobic and hydrophilic components at different concentration ranges, including hydrophilic drugs and hydrophobic excipients.

The spray drying methods of the present invention are compatible with at least most hydrophilic pharmaceutical excipients, particularly including mannitol, povidone, pectin, lactose, sodium chloride, and sodium citrate. Use of the latter three excipients is particularly preferred for powders intended for pulmonary delivery as they are "generally recognized as safe" (GRAS) for such applications. The methods are also suitable for use with numerous hydrophobic drugs and nutrients, including steroids and their salts, such as budesonide, testosterone, progesterone, estrogen, flunisolide, triamcinolone, beclomethasone, betamethasone; dexamethasone, fluticasone, methylprednisolone, prednisone, hydrocortisone, and the like; peptides, such as cyclosporin and other water insoluble peptides; retinoids, such as all-cis retinoic acid, 13-trans retinoic acid, and other vitamin A and beta carotene derivatives; vitamins D, E, and K and water insoluble precursors and derivatives thereof; prostaglandins and leukotrienes and their activators and inhibitors including prostacyclin (epoprostanol), and prostaglandins $E_1$ $E_2$; tetrahydrocannabinol; lung surfactant lipids; lipid soluble antioxidants; hydrophobic antibiotics and chemotherapeutic drugs such as amphotericin B, adriamycin, and the like.

The spray drying methods can produce a uniform particle size distribution. For example, the mean particle diameter can be controlled below 10 µm, preferably below 5 µm, with a size distribution (standard deviation) less than ±2 µm. The particles of the powders so produced have a minimum batch-to-batch variability in composition, and are physically and chemically stable. The powders have minimum residual organic solvents to the extent they may have been used in the spray drying process.

In a first aspect of the method of the present invention, an aqueous solution of the hydrophilic component is prepared, typically by mixing in water under a vacuum or reduced pressure. The hydrophobic component is then suspended in the aqueous solution of the hydrophilic component to form a suspension. The suspension is then spray dried to form particles comprising of both the hydrophilic and the hydrophobic components. Usually, the hydrophobic component will have an aqueous solubility less than 5 mg/ml, more usually below 1 mg/ml. The hydrophilic component will have a concentration in the aqueous solution in the range from 1 mg/ml to 100 mg/ml, usually from 5 mg/ml to 60 mg/ml, and the hydrophobic component is suspended in the solution to a concentration in the range from 0.01 mg/ml to 10 mg/ml, usually from 0.05 mg/ml to 5 mg/ml.

In a second aspect, the method of the present invention comprises preparing a solution of a hydrophobic component in an organic solvent. The hydrophilic component is then suspended in the organic solvent to form a suspension. The suspension is then spray dried to form particles comprising both the hydrophobic and hydrophilic components. Usually, the hydrophobic component has a solubility of at least 0.1 mg/ml, preferably being at least about 1 mg/ml. The hydrophilic component will usually have a solubility below 5 mg/ml in the organic solvent, more usually being below 1 mg/ml. In the organic suspension, the hydrophobic component preferably has a concentration in the range from 0.01 mg/ml to 10 mg/ml, more preferably from 0.05 mg/ml to 5 mg/ml, and the hydrophilic component is usually suspended to a concentration in the range from 1 mg/ml to 100 mg/ml, more usually from 5 mg/ml to 60 mg/ml. Preferred organic solvents include alcohols, ketones, hydrocarbons, and the like.

In a third aspect, the method of the present invention comprises at least partially dissolving hydrophilic component in an organic solvent or cosolvent system. The hydrophobic component is at least partially dissolved in the same organic solvent or cosolvent system to produce a solution. The organic solvent solution or cosolvent system is then spray dried to form particles comprising a mixture of the hydrophilic and hydrophobic components. The organic solvent will be selected to provide a solubility for the hydrophilic component of at least 1 mg/ml, preferably at least 5 mg/ml, and a solubility for the hydrophobic component of at least 0.01 mg/ml, preferably at least 0.05 mg/ml. Usually, the hydrophilic component will have a concentration in the organic solvent or cosolvent system solution from 1 mg/ml to 100 mg/ml, preferably from 5 mg/ml to 60 mg/ml, and the hydrophobic component will have a concentration from 0.01 mg/ml to 10 mg/ml, preferably from 0.05 mg/ml to 5 mg/ml. Suitable organic solvents or solvent systems are selected to provide such minimum solubility characteristics, but it is preferred if the organic solvent or cosolvent system provides solubilities well in excess of the stated minimums.

In a fourth aspect, the method of the present invention comprises preparing an aqueous solution of a hydrophilic component and an organic solution of a hydrophobic component in an organic solvent. The aqueous solution and the organic solution are simultaneously spray dried to form particles comprising a mixture of the hydrophilic and hydrophobic components. Usually the hydrophilic component has a concentration in the aqueous solution from 1 mg/ml to 100 mg/ml, preferably from 5 mg/ml to 60 mg/ml. The hydrophobic component has a solubility in the organic solution of at least 0.01 mg/ml, preferably at least 0.05 mg/ml. The concentration of the hydrophobic component in the organic solution is usually in the range from 0.01 mg/ml to 10 mg/ml, preferably from 0.05 mg/ml to 5 mg/ml. Preferred organic solvents include alcohols, ketones, ethers, aldehydes, hydrocarbons, and polar aprotic solvents, and the like. The use of a separate aqueous and organic solution to carry the hydrophilic and hydrophobic components, respectively, is advantageous in that it allows a much broader range of selection for the organic solvent, since the organic solvent does not also have to solubilize the hydrophilic component. Usually, the aqueous solution and organic solution will be spray dried through a common spray nozzle, more usually through a coaxial spray nozzle.

Powders prepared by any of the above methods will be collected from the spray dryer in a conventional manner for subsequent use. For use as pharmaceuticals and other purposes, it will frequently be desirable to disrupt any agglomerates which may have formed by screening or other conventional techniques. For pharmaceutical uses, the dry powder formulations will usually be measured into a single dose, and the single dose sealed into a package. Such packages are particularly useful for dispersion in dry powder inhalers, as described in detail below. Alternatively, the powders may be packaged in multiple-dose containers.

The present invention further comprises dry powder compositions produced according to the methods described above, as well as unit dose and multidose packages of such dried powder compositions containing a therapeutically effective amount of the dry powder.

The present invention further provides methods for aerosolizing a dry powder composition comprising the steps of providing an amount of dry powder composition produced by any of the methods described above and subsequently dispersing the dry powder composition into a flowing gas stream.

DETAILED DESCRIPTION

Figure 1:
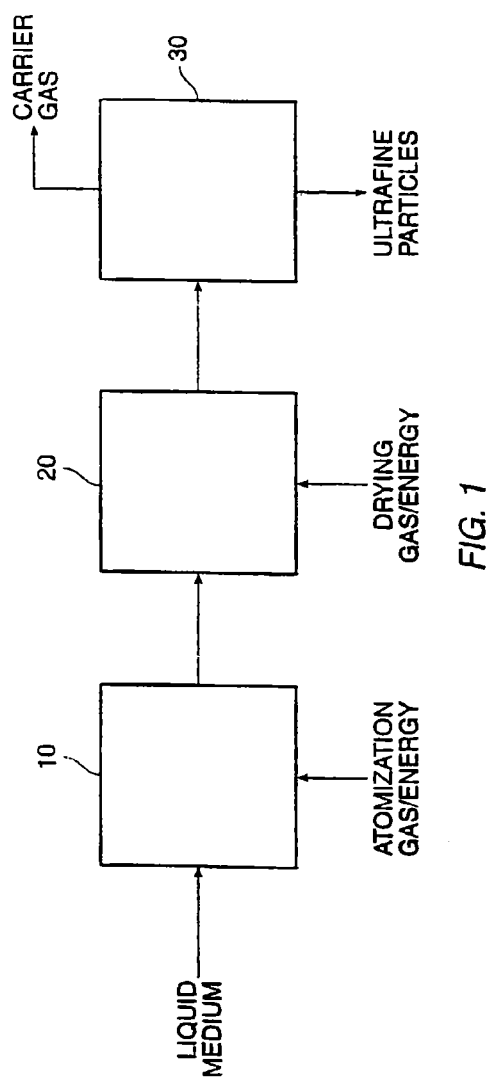
FIG. 1 is a block diagram illustrating a spray drying system suitable for performing the methods of the present invention.

The present invention relates to methods for preparing compositions comprising ultrafine dry powders having both hydrophobic and hydrophilic components. The methods are particularly suitable for producing ultrafine pharmaceutical dry powders where the hydrophobic component is a hydrophobic drug and the hydrophilic component is a hydrophilic excipient. The present invention, however, may find use for preparing a variety of other compositions intended for non-pharmaceutical applications. In all cases, the methods rely on spray drying liquid media in which the components are solubilized or suspended. In the first aspect, the hydrophilic component will be solubilized while the hydrophobic component is suspended. In the second aspect, the hydrophobic component is solubilized in an organic solvent and the hydrophilic component is suspended in that solvent. In the third aspect, an organic solvent or cosolvent system is selected which can solubilize both the hydrophobic and the hydrophilic component. In a fourth aspect, the hydrophobic and hydrophilic components are solubilized in separate liquid media and the media are simultaneously spray dried through a common nozzle. Each of these aspects has its own advantages and uses.

The term "hydrophobic component" refers to materials which are insoluble or sparingly or poorly soluble in water. As used herein, such compositions will have a solubility below 5 mg/ml, usually below 1 mg/ml. Exemplary hydrophobic drugs include certain steroids, such as budesonide, testosterone, progesterone, estrogen, flunisolide, triamcinolone, beclomethasone, betamethasone, dexamethasone, fluticasone, methylprednisolone, prednisone, hydrocortisone, and the like; certain peptides, such as cyclosporin cyclic peptide, retinoids, such as all-cis retinoic acid, 13-trans retinoic acid, and other vitamin A and beta carotene derivatives; vitamins D, E, and K and water insoluble precursors and derivatives thereof; prostagladins and leukotrienes and their activators and inhibitors including prostacyclin (epoprostanol), and prostaglandins $E_1$ $E_2$; tetrahydrocannabinol; lung surfactant lipids; lipid soluble antioxidants; hydrophobic antibiotics and chemotherapeutic drugs such as amphotericin B and adriamycin and the like.

By "hydrophilic component," it is meant that the component is highly soluble in water and frequently capable of swelling and formation of reversible gels. Typical aqueous solubilities of hydrophilic components will be greater than 5 mg/ml, usually greater than 50 mg/ml, often greater than 100 mg/ml and often much higher. In addition to their hydrophilic nature, the pharmaceutical excipients will generally be selected to provide stability, dispersibility, consistency and/or bulking characteristics to enhance the uniform pulmonary delivery of the dried powder composition to a patient. For pulmonary delivery, the excipients must be capable of being taken into the lungs with no significant adverse toxicological effects on the lungs. Exemplary hydrophilic excipients include carbohydrates and other materials selected from the group consisting of lactose, sodium citrate, mannitol, povidone, pectin, citric acid, sodium chloride, water soluble polymers, and the like. Particularly preferred are lactose, sodium chloride, sodium citrate, and citric acid which are generally accepted for pulmonary delivery in dry powder formulations.

The phrase "ultrafine dry powder" means a powder composition comprising a plurality of discrete, dry particles having the characteristics set forth below. In particular, the dry particles will have an average particle size below 10 µm, usually below 5 µm, preferably being in the range from 0.4 to 5 µm, more preferably from 0.4 to 4 µm. The average particle size of the powder will be measured as mass median diameter (MMD) by conventional techniques. A particular powder sizing technique uses a centrifugal sedimentary particle size analyzer (Horiba Capa 700). The powders will be capable of being readily dispersed in an inhalation device and subsequently inhaled by a patient so that the particles are able to penetrate into the alveolar regions of the lungs.

Of particular importance to the present invention, the ultrafine dry particle compositions produced by the method will have particle size distributions which enable them to target the alveolar region of the lung for pulmonary delivery of locally acting steroids, systemically acting proteins, and other biologically active materials that can be administered to or through the lungs. Such compositions advantageously may be incorporated into unit dosage and other forms without further size classification. Usually, the ultrafine dry powders will have a size distribution where at least 90% of the powder by weight will comprise particles having an average size in the range from 0.1 µm to 7 µm, with preferably at least 85% being in the range from 0.4 µm to 5 µm. Additionally, it is desirable that the particle size distribution avoid having an excess amount of particles with very small average diameters, i.e., below 0.4 µm.

The term "dry" means that the particles of the powder have a moisture and residual solvent content such that the powder is physically and chemically stable in storage at room temperature and is readily dispersible in an inhalation device to form an aerosol. Usually, the moisture and residual solvent content of the particles is below 10% by weight, usually being below 5% by weight, preferably being below 3% by weight, or lower. The moisture and residual solvent content will usually be controlled by the drying conditions, as described in more detail below. The term "dry" further means that the particles of the powder have a moisture and residual solvent content such that the powder is readily dispersible in an inhalation device to form an aerosol. In some cases, however, non-aqueous medium may be used for dispersing the components, in which case the aqueous content may approach zero.

The term "therapeutically effective amount" is the amount present in the composition that is needed to provide the desired level of hydrophobic drug in the subject to be treated to give the anticipated physiological response. This amount is determined for each drug on a case-by-case basis. The term "physiologically effective amount" is that amount delivered to a subject to give the desired palliative or curative effect. This amount is specific for each drug and its ultimate approval dosage level.

The therapeutically effective amount of hydrophobic drug will vary in the composition depending on the biological activity of the drug employed and the amount needed in a unit dosage form. Because the subject powders are dispersible, it is highly preferred that they be manufactured in a unit dosage form in a manner that allows for ready manipulation by the formulator and by the consumer. This generally means that a unit dosage will be between about 0.5 mg and 15 mg of total material in the dry powder composition, preferably between about 1 mg and 10 mg. Generally, the amount of hydrophobic drug in the composition will vary from about 0.01% w/w to about 95% w/w. Most preferably the composition will be about 0.05% w/w to about 25% w/w drug.

Referring now to FIG. 1, processes according to the present invention for preparing dispersible dry powders of hydrophobic and hydrophilic components comprise an atomization operation 10 which produces droplets of a liquid medium which are dried in a drying operation 20. Drying of the liquid droplets results in formation of the discrete particles which form the dry powder compositions which are then collected in a separation operation 30. Each of these unit operations will be described in greater detail below.

Figure 2:
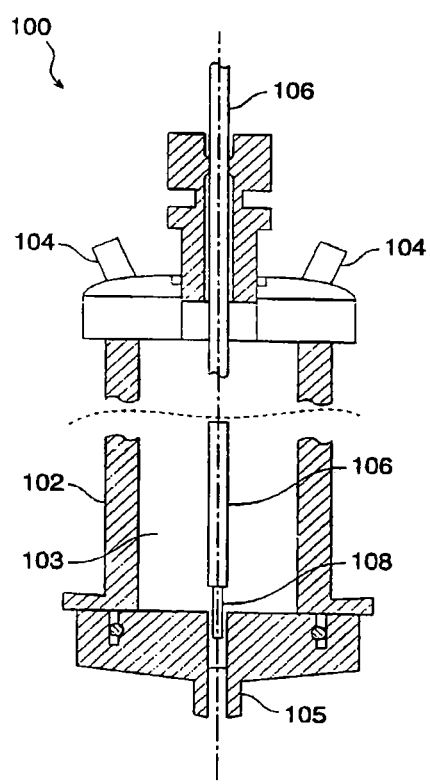
FIG. 2. illustrates a coaxial spray nozzle used in spray drying as described in the Experimental section.
Figure 3:
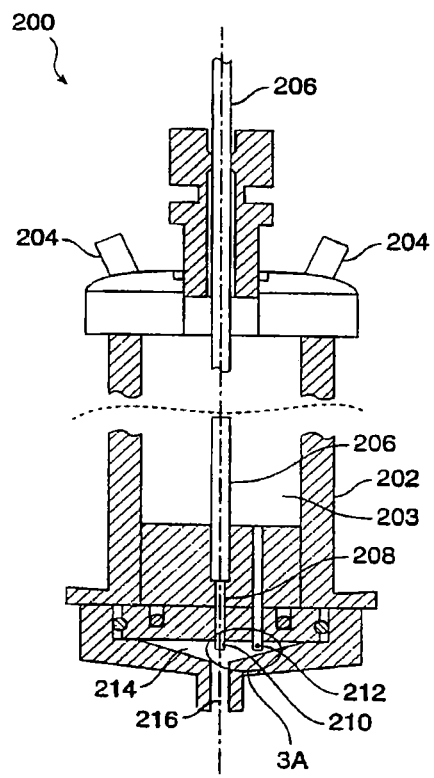
FIG. 3 illustrates a two-tube spray nozzle used in spray drying as described in the Experimental section.

The atomization process 10 may utilize anyone of several forms of atomizers, so long as the atomizer is specially designed to deliver the liquid containing the hydrophobic components and the liquid containing the hydrophilic components separately to the lower portion of the atomizer, for which FIG. 2 and FIG. 3 serve as nonlimiting examples. The atomization process increases the surface area of the starting liquid. Due to atomization there is an increase in the surface energy of the liquid, the magnitude of which is directly proportional to the surface area increase. The source of this energy increase depends on the type of atomizer used. Any atomizer (centrifugal, sonic, pressure, two fluids) capable of producing droplets with a mass median diameter of less than about 20 µm could be used. Preferred for the present invention is the use of two fluid atomizers where the liquid medium is delivered through a nozzle concurrently with a high pressure gas stream. Particularly preferred is the use of two-fluid atomization nozzles as described in copending application Ser. No. 08/644,681, which is capable of producing droplets having a median diameter less than 20 µm.

The atomization gas will usually be nitrogen which has been filtered or otherwise cleaned to remove particulates and other contaminants. Alternatively, other gases, such as air may be used. The atomization gas will be pressurized for delivery through the atomization nozzle, typically to a pressure above 5 psig, preferably being above 10 psig. Although flow of the atomization gas is generally limited to sonic velocity, the higher delivery pressures result in an increased atomization gas density. Such increased gas density has been found to reduce the droplet size formed in the atomization operation. Smaller droplet sizes, in turn, result in smaller particle sizes. The atomization conditions, including atomization gas flow rate, atomization gas pressure, liquid flow rate, and the like, will be controlled to produce liquid droplets having an average diameter below 20 µm as measured by phase doppler velocimetry.

The drying operation 20 will be performed next to evaporate liquid from the droplets produced by the atomization operation 10. Usually, the drying will require introducing energy to the droplets, typically by mixing the droplets with a heated gas which causes evaporation of the water or other liquid medium. Preferably, the heated gas stream will flow concurrently with the atomized liquid, but it would also be possible to employ counter-current flow, cross-current flow, or other flow patterns.

The drying rate may be controlled based on a number of variables, including the droplet size distribution, the inlet temperature of the gas stream, the outlet temperature of the gas stream, the inlet temperature of the liquid droplets, and the manner in which the atomized spray and hot drying gas are mixed. Preferably, the drying gas stream will have an inlet temperature of at least 70° C. The outlet temperature will usually be at least about 40° C. The drying gas will usually be air or nitrogen which has been filtered or otherwise treated to remove particulates and other contaminants. The gas will be moved through the system using conventional blowers or compressors.

The separation operation 30 will be selected in order to achieve very high efficiency collection of the ultrafine particles produced by the drying operation 20. Conventional separation operations may be used, although in some cases they should be modified in order to assure collection of sub-micron particles. In an exemplary embodiment, separation is achieved using a filter medium such as a membrane medium (bag filter), a sintered metal fiber filter, or the like. Alternatively, and often preferably, separation may be achieved using cyclone separators, although it is usually desirable to provide for high energy separation in order to assure the efficient collection of sub-micron particles. The separation operation should achieve collection of at least 80% of all particles above 1 µm in average particle size, preferably being above 85%, more preferably being above 90%, and even more preferably being above 95%, in collection efficiency.

Figure 3A:
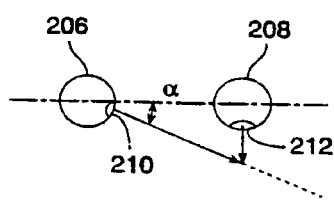
FIG. 3A is a detail cross-section view of region 3A in FIG. 3.

In some cases, a cyclone separator can be used to separate very fine particles, e.g. 0.1 µm, from the final collected particles. The cyclone operating parameters can be selected to provide an approximate cutoff where particles above about 0.1 µm are collected while particles below 0.1 µm are carried over in the overhead exhaust. The presence of particles below 0.1 µm in the pulmonary powder is undesirable since they will generally not deposit in the alveolar regions of the lungs, but instead will be exhaled.

The present invention relies on proper selection of the liquid medium or media for suspending hydrophobic drug or other component and hydrophilic excipient or other component. In the first aspect, the liquid medium will be water which will fully dissolve the hydrophilic excipient or other component to form a solution. The hydrophobic component is then suspended in the solution, and the solution spray dried as described above to form a powder having particles comprising a mixture of the dried hydrophilic and hydrophobic component. This approach is advantageous in that it avoids the use of organic solvents. It is important, however, that the hydrophobic drug be adequately suspended in the mixing vessel and in the supply lines to the spray dryer so that there is minimum loss from the aqueous medium prior to spray drying. It is also important that the hydrophobic drug be in a powder form with an average particle size below 5 µm, preferably below 4 µm, and even more preferably below 2.5 µm to minimize the preferential accumulation of drugs in certain individual particles.

In the second aspect of the present invention, the hydrophobic drug or other component is dissolved in an organic solvent selected to fully dissolve the drug. The hydrophilic excipient is insoluble or sparingly soluble in the organic solvent, and is formed into a powder and suspended in the organic solvent. The resulting liquid medium is then spray dried as described above. This approach is advantageous in that the hydrophilic excipient may be wholly or partially coated with the hydrophobic drug. Such a coating can, in some instances, enhance the surface characteristics of the particles to improve handling and/or aerosolization characteristics. For example, coating budesonide over a carrier such as lactose has been found to reduce particle agglomeration sufficiently to eliminate the need to disrupt agglomerates (e.g. by screening) prior to packaging, thus reducing manufacturing cost.

According to the third aspect of the present invention. an organic solvent or cosolvent is selected in which both the hydrophobic drug or other component and the hydrophilic excipient or other component may be dissolved. Neither the drug nor excipient need be highly soluble in the solvent, since both components will typically be present in the solvent at relatively low concentrations, usually below 10% w. more usually below 5% w. The solvent must further be selected to leave minimum residual solvent in the spray dried process and/or be capable of being adequately removed from the spray dried product. The particular organic solvent or cosolvent selected will depend on the nature of the hydrophobic drug and the hydrophilic excipient. Exemplary combinations of drug, excipient, and solvent are set forth in Table 1 below.

TABLE 1

| DRUG | EXCIPIENT | SOLVENT |
|---|---|---|
| Budesonide (good solubility) | Povidone (highly soluble) | Methanol |
| Budesonide (adequate solubility) | Povidone (good solubility) | Ethanol |
| Budesonide (adequate solubility) | Mannitol (adequate solubility) | Acetone (50%)/ Water (50%) (by volume) |
| Budesonide (good solubility) | Lactose (adequate solubility) | DMSO (33%)/ Acetone (67%) (by volume) |

Each of these formulations has been spray dried and tested as described in further detail in the Experimental section hereinafter. It should be noted that for many pharmaceutical compositions, it will be desirable to provide the excipient at significantly higher concentrations than the drug. Thus, when choosing a common solvent system as in the third aspect of the present invention, it may be necessary to choose solvents which provide for greater solubility for the excipient than for the drug.

The spray drying methods which employ a common solubilizing solvent system are advantageous in that both the hydrophobic drug or other component and the hydrophilic excipient or other component will be fully dissolved, enhancing product uniformity after spray drying. The full dissolution of the component is desirable since it greatly reduces the likelihood that the components will separate to any significant extent during storage, delivery to the spray drier, passage through the spray nozzle, or during the spray drying operation.

In the fourth aspect of the present invention, the compositions are spray dried by forming separate solutions of the hydrophobic drug or other component and the hydrophilic excipient or other component. The separate solutions are then concurrently separately spray dried, typically by passing through a common spray nozzle or nozzles in the spray driers described above. This method has the advantage that both the hydrophobic drug and the hydrophilic excipient may be easily dissolved since it is generally straight forward to select compatible solvents capable of fully dissolving only one of the components. By properly directing the two solutions through a nozzle, such as a coaxial nozzle, spray dried powders having uniform characteristics may be achieved. This approach has an additional advantage that it minimizes the amount of organic solvent required since only the hydrophobic drug or other component requires an organic solvent for dissolution. The hydrophilic excipient is dissolved in water.

An exemplary coaxial spray nozzle 100 is illustrated in FIG. 2 and includes a housing 102 defining a chamber 103. A pair of inlets 104 is disposed at the top of the housing 102 for receiving the excipient solution (which is usually delivered at a higher volumetric flow rate than is the solution of the hydrophobic component). The excipient solution enters the chamber 103 at a pressure sufficient to achieve a desired flow rate through an outlet orifice 105 at the bottom of the housing 102. The hydrophobic component solution is fed through a feed tube 106 which usually terminates in a reduced diameter section 108 which is disposed coaxially within the orifice 105. The absolute and relative sizes of the orifice 105 and section 108 of feed tube 106 will depend on the total flow rates, operating pressures, and nature of materials being spray dried. A specific example is described in the Experimental section hereinafter.

A second exemplary spray nozzle 200 is illustrated in FIGS. 3 and 3A. The nozzle 200 comprises a housing 202, inlets 204 and feed tube 206, generally similar to those described above for nozzle 100. Nozzle 200, however, is not coaxial and instead includes a second, parallel feed tube 208 which receives solution from chamber 203 defined within the housing 202. Both the feed tube 206 and feed tube 208 have outlet orifices 210 and 212, respectively, at their distal ends which direct the solution flow generally horizontally into a mixing chamber 214 disposed at the bottom of the housing 202. The mixing chamber is shown to have a conical geometry terminating aL its bottom tip in outlet passage 216. The orifices 210 and 212 are preferably oriented as shown in FIG. 3A where the relative angle a is in the range from 5° to 25°, usually about 10°. Such an orifice arrangement results in a vertical mixing flow in the chamber 214 prior to ejection from the passage 216. A variety of other mixing chamber designs could also be utilized.

Once the dry powders have been prepared, they may be packaged in conventional ways. For pulmonary pharmaceutical applications, unit dosage forms may comprise a unit dosage receptacle containing a dry powder. The powder is placed within a suitable dosage receptacle in an amount sufficient to provide a subject with drug for a unit dosage treatment. The dosage receptacle is one that fits within a suitable inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. No. 4,227,522 issued Oct. 14, 1980; U.S. Pat. No. 4,192,309 issued Mar. 11, 1980; and U.S. Pat. No. 4,105,027 issued Aug. 8, 1978. Suitable containers also include those used in conjunction with Glaxo's VENTOLIN ROTO-HALER® brand powder inhaler or Fison's SPINHALER® brand powder inhaler. Another suitable unit-dose container which provides a superior moisture barrier is formed from an aluminum foil plastic laminate. The pharmaceutical-based powder is filled by weight or by volume into the depression in the formable foil and hermetically sealed with a covering foil-plastic laminate. Such a container for use with a powder inhalation device is described in U.S. Pat. No. 4,778,054 and is used with Glaxo's DISKHALER® (U.S. Pat. Nos. 4,627,432; 4,811,731; and 5,035,237). Preferred dry powder inhalers are those described in U.S. patent application Ser. Nos. 08/309,691 and 08/487,184, assigned to the assignee of the present invention. The latter application has been published as WO 96/09085.

The following examples are offered by way of illustration, not by way of limitation.

EXPERIMENTAL

The following materials were used:
Budesonide (micronized to a median particle size of 1-2 μm; Steraloids)
Lactose monohydrate (NF grade; Foremost Ingredient Group)
Spray dried lactose (median particle size of 1-3 μm)
Jet milled lactose
Povidone (PVP K-15; ISP Technologies)
Mannitol (USP grade; Mallinckrodt)
Sodium Chloride (reagent grade from VWR and USP grade from EM Industries)
Spray dried sodium chloride
Sodium cilrate, dihydrate (USP grade; Mallinckrodt)
Spray dried sodium citrate
Deionized water
Ethanol, 200 proof (USP/NF; Spectrum Chemical Mfg. Corp.)
Acetone (for histology; EM Industries)
Methanol (HPLC grade; EM Industries)
Dimethyl sulfoxide (DMSO; Photex reagent grade; J. T. Baker)

All batches were spray dried on Buchi 190 Mini Spray Dryers, with nozzles and cyclones that were designed to generate and catch very fine particles. For formulations that utilized organic solvents, a modified Buchi 190 Mini Spray Dryer was used that was supplied with nitrogen as the gas source and equipped with an oxygen sensor and other safely equipment to minimize the possibility of explosion. The solution feed rate was 5 ml/minute, inlet temperature was adjusted to obtain the outlet temperature noted in each example, the top of the cyclone was jacketed and cooled to a temperature of about 30° C., the drying air (or nitrogen) flow rate was about 18 SCFM, and the atomizing air was supplied at 0.5 to 1.5 SCFM. The powders were further dried in the collector for 5-15 minutes (most often for 5 minutes) by maintaining approximately the outlet temperature and air volume after the feeding of the liquid formulation was completed.

Particle size was determined with a Horiba Particle Size Analyzer, model CAP A 700. Median particle size refers to the volume based particle size distribution of the prepared bulk powders determined via centrifugal sedimentation as follows. A sample of the powder was suspended in an appropriate liquid medium (one that minimizes solubilizing the particle), sonicated to break up the agglomerates, and then centrifuged. The median particle size was determined by measuring the sedimentation rate during centrifugation. This method provides the median size of the "primary" particle, that is, the size of the particles produced by the manufacturing process, plus potential modification during sample preparation. Because these formulations are composed of both water soluble and water insoluble materials, it is likely that the suspension step during sample preparation does to some extent solubilize part of the particle, and thereby modify the particle size that is determined. Therefore, the resultant particle sizes should be viewed as estimated values, rather than absolute values.

Moisture content was determined by the Karl-Fischer Reagent titrimetric method.

Delivered dose efficiency refers to a measure of the percentage of powder which is drawn out of a blister package and which exits the mouthpiece of an inhaler device as described in U.S. patent application Ser. No. 08/487,184. Delivered dose efficiency is a measure of efficiency for the powder package/device combination. The test was performed by connecting a vacuum system to the device mouthpiece. The vacuum system was set to be similar to a human inhalation with regard to volume and flow rate (1.2 liters total at 30 liters/minute). A blister package containing 0.5 to 10 mg of the formulation to be evaluated (5 mg of powder was used for the following examples) was loaded into a device which is held in a testing fixture. The device was pumped and fired, and the vacuum "inhalation" is switched on. The aerosol cloud was thus drawn out of the device chamber by the vacuum, and the powder was collected on a filter placed between the mouthpiece and the vacuum source. The weight of the powder collected on the filter was determined. Delivered dose efficiency was calculated this weight, multiplied by one hundred, divided by the fill weight in the blister. A higher number is a better result than a lower number.

1. Suspending Budesonide in Aqueous Excipient Solutions
Manufacturing Procedure:

If the formulation required the inclusion of any organic solvent as a manufacturing aid, the organic solvent was mixed with the water. The budesonide and excipient(s) were mixed with the liquid medium to form a suspension of the budesonide, with the excipients dissolved in the liquid medium. Continue mixing the suspension prior to and throughout spray drying. Spray dry the suspension. The powders were then passed through a screen (a 35 mesh screen was used). This last step may not always be required, but it has been found that passing the powders through a screen will often decrease the blister to blister delivered dose efficiency variability.

Many different mixing techniques for preparation of the suspension have been and may be used, but one that has been found to be particularly useful (to reduce the creation of foam and deposition of drug substance on the mixing vessel walls) was to weigh the powders into the mixing vessel, add half of the liquid medium, deaerate the mixture under vacuum, then mix the excipients and the liquid medium with a magnetic stirrer under the vacuum, sonicate the resulting suspension while maintaining the vacuum, slowly release the vacuum and add the rest of the liquid medium (rinse down the container walls while doing so), pull a vacuum again and deaerate the suspension, stir it again and then sonicate it again (all under vacuum), and then slowly release the vacuum and continue mixing the suspension prior to and throughout spray drying, being careful to not incorporate air into the suspension.

Table 2, below, shows the spray drier atomization air pressure and outlet air temperature, the quantitative composition of example formulations, a description of the particle morphology, the moisture content, particle size, and delivered dose efficiency of the resultant powders. Where the powders have been passed through a 35 mesh screen, the delivered dose efficiency results are preceded by the word "screened."

TABLE 2

Suspending budesonide in aqueous excipient solutions

| Batch No., Formula No. (Spray Drier Atomization Air Pressure/Outlet Air Temperature) | Quantitative Composition | | Particle Morphology | Moisture Content | Particle Size (μm) | Delivered Dose Efficiency | |
|---|---|---|---|---|---|---|---|
| 329-8 | Budesonide | 50 mg | Smooth spheres | 1.93% | 2.32 | | 41.5% (RSD = 13) |
| B-1 | Lactose | 950 mg | | | | Screened: | 41.3% (RSD = 15) |
| (40PSI/77° C.) | DI water | 100 ml | | | | | |
| 329-9 | Budesonide | 50 mg | Spheres made up | 0.88% | 1.50 | | 41.1% (RSD = 15) |
| B-2 | Sodium Chloride | 950 mg | of small cubes | | | Screened: | 43.2% (RSD = 7) |
| (40PSI/77° C.) | DI water | 100 ml | | | | | |
| 329-61 | Budesonide | 350 mg | | 0.91% | 1.57 | Screened: | 34.5% (RSD = 9) |
| B-2 | Sodium Chloride | 6650 mg | | | | | |
| (40PSI/77° C.) | DI water | 700 ml | | | | | |
| 329-10 | Budesonide | 49 mg | Smooth spheres | 4.23% | 2.74 | | 52.6% (RSD = 10) |
| B-3 | Sodium Citrate | 949 mg | | | | Screened: | 52.4% (RSD = 9) |
| (40PSI/80° C.) | DI water | 100 ml | | | | | |
| 329-11 | Budesonide | 49 mg | Smooth spheres | 2.00% | 2.45 | | 53.0% (RSD = 20) |
| B-4 | Lactose | 317 mg | | | | Screened: | 70.7% (RSD = 4) |
| (40PSI/79° C.) | Sodium Chloride | 317 mg | | | | | 56.2% (RSD = 10) |
| | Sodium Citrate | 316 mg | | | | | upon retesting |
| | DI water | 100 ml | | | | | |
| 329-60 | Budesonide | 350 mg | | 2.07% | 2.04 | Screened: | 53.2% (RSD = 9) |
| B-4 | Lactose | 2217 mg | | | | | |
| (40PSI/79° C.) | Sodium Chloride | 2217 mg | | | | | |
| | Sodium Citrate | 2216 mg | | | | | |
| | DI water | 700 ml | | | | | |
| 329-35-S | Budesonide | 50 mg | Smooth spheres | 0.82% | 2.37 | Screened: | 57.3% (RSD = 4) |
| B-7 | Lactose | 475 mg | | | | | |
| (40PSI/77° C.) | Sodium Chloride | 475 mg | | | | | |
| | DI water | 100 ml | | | | | |
| 329-69-S | Budesonide | 350 mg | | 1.00% | 2.16 | Screened: | 59.5% (RSD = 9) |
| B-7 | Lactose | 3325 mg | | | | | |
| (40PSI/77° C.) | Sodium Chloride | 3325 mg | | | | | |
| | DI water | 700 ml | | | | | |
| 329-73-S | Budesonide | 350 mg | | 1.02% | 1.78 | Screened: | 63.3% (RSD = 8) |
| B-7 | Lactose | 3325 mg | | | | | |
| (40PSI/77° C.) | Sodium Chloride | 3325 mg | | | | | |
| | DI water | 700 ml | | | | | |
| 329-56 | Budesonide | 50 mg | | 0.79% | 2.05 | | 62.3% (RSD = 19) |
| B-20 | Lactose | 475 mg | | | | | |
| (40PSI/78° C.) | Sodium Chloride | 475 mg | | | | | |
| | 95:5 water:acetone | 100 ml | | | | | |
| 329-58 | Budesonide | 50 mg | | 0.70% | 1.88 | | 55.7% (RSD = 19) |
| B-22 | Lactose | 475 mg | | | | | |
| (40PSI/77° C.) | Sodium Chloride | 475 mg | | | | | |
| | 95:5 water:methanol | 100 ml | | | | | |
| 329-36-S | Budesonide | 50 mg | Rough surfaced | 1.91% | 2.01 | Screened: | 44.2% (RSD = 7) |
| B-8 | Sodium Chloride | 475 mg | spheres | | | | |
| (40PSI/80° C.) | Sodium Citrate | 475 mg | | | | | |
| | DI water | 100 ml | | | | | |
| 329-37-S | Budesonide | 50 mg | Smooth spheres | 2.20% | 1.79 | Screened: | 44.1% (RSD = 6) |
| B-9 | Lactose | 475 mg | | | | | |
| (40PSI/80° C.) | Sodium Citrate | 475 mg | | | | | |
| | DI water | 100 ml | | | | | |

2. Suspending Excipient in an Organic Solvent Budesonide Solution

Manufacturing Procedure:

The budesonide was mixed with the organic solvent until all of the budesonide was completely dissolved to form a solution (sonicate if necessary aid dissolution of the solids). The budesonide solution was mixed with the excipient(s) to form a suspension, and then sonicated. The suspension was continuously mixed prior to and throughout spray drying. It was found that passing these powders through a screen (e.g. a 35 mesh screen as used in the example) was usually not required.

Table 3 shows the spray drier atomization air pressure and outlet air temperature, quantitative composition, a description of the particle morphology, particle size, and delivered dose efficiency for each powder. Where the powder was passed through a 35 mesh screen. the delivered dose efficiency results are preceded by the word "screened." It appears using spray dried lactose as the excipient results in the best delivered dose efficiency, and that switching spray dried lactose with either jet milled lactose, sodium chloride, or sodium citrate results in a lower delivered dose efficiency.

3. Solubilizing Both Budesonide and Excipient in an Organic Solvent System

Manufacturing Procedure:

The indicated amounts of the budesonide and the excipient(s) were mixed with the indicated amount of the liquid medium until all of the solids were completely dissolved to form a solution. If necessary the solutions were sonicated to fully dissolve the solids. The solutions were spray dried, and the resulting powders passed through a 35 mesh screen. This last step may not always be required, but it has been found that passing the powders through a screen will often decrease the delivered dose efficiency variability.

Table 4 shows the spray drier atomization air pressure and outlet air temperature, the quantitative composition, a description of the particle morphology, the moisture content where water was a component in the liquid medium, particle size, and delivered dose efficiency for each powder. Where the powders were passed through a 35 mesh screen, the delivered dose efficiency results are preceded by the word "screened." It is noteworthy that the use of a 1:2 DMSO/acetone liquid medium yielded low delivered dose efficiency results.

TABLE 3

Suspend excipient in an organic solvent budesonide solution

| Batch No., Formula No., (Spray Drier Atomization Air Pressure/ Outlet Air Temp.) | Quantitative Composition | | Particle Morphology | Particle Size (μm) | Delivered Dose Efficiency |
|---|---|---|---|---|---|
| 329-32 B-6 (20PSI/66° C.) | Budesonide Spray dried lactose Ethanol | 75 mg 1425 mg 50 ml | | 1.85 | 40.7% (RSD = 9) |
| 329-33 B-6 (40PSI/65° C.) | Budesonide Spray dried lactose Ethanol | 75 mg 1425 mg 50 ml | Agglomerations of minute crystals | 3.12 | 54.5% (RSD = 3) (Yield = 55%) |
| 329-64 B-6 (40PSI/65° C.) | Budesonide Spray dried lactose Ethanol | 350 mg 6650 mg 233 ml | | 2.92 | 40.6% (RSD = 10) retest: 39.4% (RSD = 13) Screened: 45.1% (RSD = 11) |
| 329-41 B-11 (40PSI/65° C.) | Budesonide Jet milled lactose Ethanol | 25 mg 475 mg 50 ml | Rectangular needles | 1.77 | 43.2% (RSD = 8) |
| 329-48 B-15 (40PSI/67° C.) | Budesonide Spray dried lactose Methanol | 75 mg 1477 mg 50 ml | Plates | 1.50 | 38.6% (RSD = 10) |
| 329-49 B-16 (40PSI/68° C.) | Budesonide Spray dried lactose Acetone | 75 mg 1425 mg 50 ml | Plates | 1.49 | 45.3% (RSD = 5) |
| 329-50 B-17 (40PSI/66° C.) | Budesonide Jet milled lactose Ethanol | 75 mg 1425 mg 50 ml | Mesh of needles | 0.78 | 11.4% (RSD = 44) |
| 329-55 B-19 (40PSI/66° C.) | Budesonide Spray dried sodium chloride Ethanol | 75 mg 1425 mg 50 ml | | 3.52 | 21% (RSD = 18) |
| 329-72 B-23 (20PSI/66° C.) | Budesonide Spray dried sodium chloride Ethanol | 75 mg 1425 mg 50 ml | | 2.30 | 27.1% (RSD = 51) |

TABLE 4

Solubilizing both budesonide and excipient in an organic solvent system

| Batch No., Formula No. (Spray Drier Atomization Air Pressure/Outlet Air Temperature) | Quantitative Composition | | Particle Morphology | Moisture Content | Particle Size (μm) | Delivered Dose Efficiency |
|---|---|---|---|---|---|---|
| 329-20 B-51 (15PSI/57° C.) | Budesonide Mannitol 1:1 Acetone:DI water | 75 mg 1425 mg 50 ml | Slightly dimpled spheres | 0.49% | 2.31 | 47.2% (RSD = 12) Screened: 55.4% (RSD = 7) retest: 51.2% (RSD = 10) retest: 52.2% (RSD = 13) |

TABLE 4-continued

Solubilizing both budesonide and excipient in an organic solvent system

| Batch No., Formula No. (Spray Drier Atomization Air Pressure/Outlet Air Temperature) | Quantitative Composition | | Particle Morphology | Moisture Content | Particle Size (μm) | Delivered Dose Efficiency | |
|---|---|---|---|---|---|---|---|
| 329-59 B-51 (15PSI/57° C.) | Budesonide Mannitol 1:1 Acetone:DI water | 350 mg 6650 mg 233 ml | | 0.51% | 2.35 | Screened: | 47.9% (RSD = 11) |
| 329-79 B-51 (15PSI/57° C.) | Budesonide Mannitol 1:1 Acetone/DI water | 350 mg 6650 mg 233 ml | | 0.50% | 1.93 | Screened: | 52.1% (RSD = 9) |
| 329-22 B-52 (20PSI/66° C.) | Budesonide PVP K-15 Ethanol | 75 mg 1425 mg 50 ml | | No water in formula | 3.59 | | 44.8% (RSD = 20) |
| 329-23 B-52 (15PSI/76° C.) | Budesonide PVP K-15 Ethanol | 75 mg 1425 mg 50 ml | Dimpled spheres | No water in formula | 3.39 | | 50.2% (R5D = 22) |
| 329-46 B-52 (15PSI/76° C.) | Budesonide PVP K-15 Ethanol | 75 mg 1425 mg 50 ml | Dimpled spheres | No water in formula | 1.09 | Screened: | 49.8% (RSD = 28) 60.5 (RSD = 7) |
| 329-62 B-52 (15PSI/76° C.) | Budesonide PVP K-15 Ethanol | 350 mg 6650 mg 233 ml | | No water in formula | 2.51 | Screened: | 43.7% (RSD = 13) |
| 329-78-S B-52 (15PSI/76° C.) | Budesonide PVP K-15 Ethanol | 350 mg 6650 mg 233 ml | | No water in formula | 2.26 | Screened: | 44.8% (RSD = 9) |
| 329-25 B-53 (20PSI/66° C.) | Budesonide PVP K-15 Methanol | 75 mg 1425 mg 50 ml | Dimpled spheres | No water in formula | Not available | Screened: | 46.3% (RSD = 14) 35.6% (RSD = 8) |
| 329-30 B-5 (15PSI/68° C.) | Budesonide Lactose 1:2 DMSO:acetone | 75 mg 1425 mg 75 ml | | No water in formula | 4.15 | | 13.6% (RSD = 30) |
| 329-31 B-5 (10PSI/73° C.) | Budesonide Lactose 1:2 DMSO:acetone | 75 mg 1425 mg 75 ml | Plates | No water in formula | Not available | | 6.5% (RSD = 45) |

4. Coaxial Nozzle System:

Manufacturing Procedure:

The budesonide was mixed in the organic solvent until all of the budesonide was completely dissolved to form a solution, with sonication if necessary. The excipient was mixed with the water until all of the excipient was completely dissolved to form a solution, with sonication, if necessary. The solutions were spray dried using a coaxial nozzle spray drying system having a nozzle as illustrated in FIG. 2, where orifice 105 has a diameter of 1.0 mm and outlet tube section 108 has an outside diameter of 0.73 mm and an inside diameter of 0.6 mm.

The two solutions should be fed to the nozzle at constant rates such that they both finish being fed to the nozzle at the same time.

Table 5 shows the spray drier atomization air pressure and outlet air temperature, the quantitative composition of example formulations, a description of the particle morphology, the moisture content, particle size. and delivered dose efficiency of the resultant powders.

TABLE 5

| Batch No., Formula No. (Spray Dryer Atomization Air Pressure/Outlet Air Temperature) | Quantitative Composition | | Particle Morphology | Moisture Content | Particle Size (μm) | Delivered Dose Efficiency |
|---|---|---|---|---|---|---|
| 329-44 B-13 (20PSI/76° C.) | Budesonide Ethanol Lactose DI water | 75 mg 25 ml 1425 mg 25 ml | Slightly wrinkled spheres | 0.76% | 2.11 | 42.0% (RSD = 25) |
| 329-47 B-14 (40PSI/77° C.) | Budesonide 9:1 Acetone:water Lactose DI water | 50 mg 1.25 ml 950 mg 98.75 ml | | 1.09% | 1.99 | 49.5% (RSD = 16) |

While the foregoing is directed to embodiments of the present invention, other and further embodiments of the invention may be devised without departing from the basic scope thereof, and the scope thereof is determined by the claims that follow.

The invention claimed is:

1. A dry powder drug composition in the form of a unit dose, the composition comprising discrete particles having an average particle size of less than 10 μm for delivery to the lungs as a dry powder, wherein each discrete particle comprises a drug component, a hydrophobic component having a water solubility of less than 5 mg/mL, and a hydrophilic component having a water solubility of greater than 5 mg/mL, wherein the unit dose is contained in a unit dose receptacle that is insertable into a dry powder inhaler.

2. The dry powder drug composition of claim 1, wherein the hydrophilic component comprises water soluble polymer or water soluble carbohydrate.

3. The dry powder drug composition of claim 1, wherein the hydrophilic component comprises a material selected from the group consisting of polyvinylpyrrolidone, lactose, sodium citrate, mannitol, pectin, povidone, citric acid, sodium chloride, salts thereof, and hydrates thereof.

4. The dry powder drug composition of claim 1, wherein at least about 90% by weight of the particles have the average particle size within a range from about 0.1 µm to about 7 µm.

5. The dry powder drug composition of claim 1, wherein the average particle size is within a range from about 0.4 µm to about 4 µm.

6. The dry powder drug composition of claim 1, wherein the hydrophilic component comprises a citrate.

7. The dry powder drug composition of claim 6, wherein the hydrophilic component comprises sodium citrate.

8. The dry powder drug composition of claim 1, wherein at least about 90% by weight of the particles have the average particle size within a range from about 0.1 µm to about 7 µm.

9. The dry powder drug composition of claim 8, wherein at least about 85% by weight of the particles have the average particle size within a range from about 0.4 µm to about 5 µm.

10. The dry powder drug composition of claim 9, wherein the water solubility of the hydrophilic component is greater than 50 mg/mL.

11. The dry powder drug composition of claim 10, wherein the water solubility of the hydrophilic component is greater than 100 mg/mL.

12. The dry powder drug composition of claim 1, wherein the discrete particles comprise spray-dried particles.

13. The dry powder drug composition of claim 1, where the discrete particles having an average particle size within a range from about 0.4 µm to about 5 µm for at least about 85% by weight of the particles for delivery to the lungs as a dry powder and wherein the hydrophilic excipient has a water solubility of greater than 50 mg/mL.

14. The dry powder drug composition of claim 13, wherein the water solubility of the hydrophobic component is less than 1 mg/mL.

15. The dry powder drug composition of claim 13, wherein the water solubility of the hydrophilic excipient is greater than 100 mg/mL.

16. The dry powder drug composition of claim 15, wherein the water solubility of the hydrophobic component is less than 1 mg/mL.

17. The dry powder drug composition of claim 13, wherein the discrete particles comprise spray-dried particles.

18. The dry powder drug composition of claim 1, wherein the hydrophobic component has a water solubility of less than 1 mg/mL.

19. The dry powder drug composition of claim 18, wherein the discrete particles comprise spray-dried particles.

20. The dry powder drug composition of claim 1, wherein the drug component comprises a hydrophobic drug having a water solubility of less than 5 mg/mL.

21. The dry powder drug composition of claim 20, wherein the drug component comprises one or more drugs selected from the group consisting of budesonide, testosterone, progesterone, estrogen, flunisolide, triamcinolone, beclomethasone, betamethasone, dexamethasone, fluticasone, methylprednisolone, prednisone, hydrocortisone, cyclosporin, all-cis retinoic acid, 13-trans retinoic acid, vitamin D, vitamin E, vitamin K, a prostaglandin, a leukotriene, prostacyclin, tetrahydrocannabinol, a lung surfactant lipid, a lipid soluble antioxidant, a hydrophobic antibiotic, a hydrophobic chemotherapeutic drug, amphotericin B, and adriamycin.

22. The dry powder drug composition of claim 1, wherein the drug component comprises a hydrophilic drug having a water solubility of greater than 5 mg/mL.

23. The dry powder drug composition of claim 1, wherein the unit dose receptacle comprises a capsule.

24. The dry powder drug composition of claim 23, wherein the capsule is made or gelatin or plastic.

25. The dry powder drug composition of claim 1, wherein the unit dose receptacle comprises a foil layer.

26. A dry powder drug composition comprising discrete particles having an average particle size of less than 10 µm for delivery to the lungs as a dry powder, wherein each discrete particle comprises a hydrophobic component having a water solubility of less than 5 mg/mL, a hydrophilic component having a water solubility of greater than 5 mg/mL, and a chloride salt.

27. The dry powder drug composition of claim 26, wherein each discrete particle further comprises a salt of an acid.

28. The dry powder drug composition of claim 27, wherein the salt of an acid comprises a citrate.

29. The dry powder drug composition of claim 26 wherein the chloride salt comprise sodium chloride.

30. A dry powder drug composition comprising discrete particles having an average particle size of less than 10 µm for delivery to the lungs as a dry powder, wherein each discrete particle comprises a hydrophobic component having a water solubility of less than 5 mg/mL, a hydrophilic component having a water solubility of greater than 5 mg/mL, and a salt of an acid.

31. The dry powder drug composition of claim 30, wherein the salt of an acid comprises a citrate.

\* \* \* \* \*